(12) United States Patent
Soletti et al.

(10) Patent No.: US 10,076,427 B2
(45) Date of Patent: Sep. 18, 2018

(54) GRAFT DEVICES AND RELATED SYSTEMS AND METHODS

(71) Applicant: Neograft Technologies, Inc., Taunton, MA (US)

(72) Inventors: Lorenzo Soletti, Pittsburgh, PA (US); Mohammed S. El-Kurdi, Mansfield, MA (US); Jon McGrath, Duxbury, MA (US); J. Christopher Flaherty, Topsfield, MA (US)

(73) Assignee: Neograft Technologies, Inc., Taunton, MA (US)

( * ) Notice: Subject to any disclaimer, the term of this patent is extended or adjusted under 35 U.S.C. 154(b) by 0 days.

(21) Appl. No.: 15/431,311

(22) Filed: Feb. 13, 2017

(65) Prior Publication Data

US 2017/0312100 A1 Nov. 2, 2017

Related U.S. Application Data

(63) Continuation of application No. 14/586,419, filed on Dec. 30, 2014, now Pat. No. 9,603,729, which is a
(Continued)

(51) Int. Cl.
*A61F 2/82* (2013.01)
*A61L 27/56* (2006.01)
(Continued)

(52) U.S. Cl.
CPC ............ *A61F 2/82* (2013.01); *A61B 17/11* (2013.01); *A61B 17/122* (2013.01); *A61F 2/06* (2013.01);
(Continued)

(58) Field of Classification Search
CPC .. A61F 2/06; A61F 2/062; A61F 2/064; A61F 2/82; A61F 2/91; A61F 2/07; A61F 2002/075

See application file for complete search history.

(56) References Cited

U.S. PATENT DOCUMENTS 6,015,431 A 1/2000 Thornton et al.
6,165,212 A 12/2000 Dereume et al.
(Continued)

FOREIGN PATENT DOCUMENTS

AU 2010339931 A1 7/2012
WO WO-9401056 A1 1/1994
(Continued)

OTHER PUBLICATIONS

Ayres, et al. Modulation of anisotropy in electrospun tissue-engineering scaffolds: Analysis of fiber alignment by the fast Fourier transform. Biomaterials 27 (2006) 5524-5534.
(Continued)

*Primary Examiner* — Jason-Dennis Stewart
(74) *Attorney, Agent, or Firm* — Wilson Sonsini Goodrich & Rosati

(57) ABSTRACT

In some aspects, graft devices for a mammalian patient can include a tubular member comprising a first end; and a fiber matrix surrounding the tubular member, wherein the fiber matrix is designed and constructed to be substantially continuously tapered at the first end to define a diameter that increases as it approaches the first end.

20 Claims, 8 Drawing Sheets

Related U.S. Application Data continuation of application No. 13/515,996, filed as application No. PCT/US2010/060667 on Dec. 16, 2010, now Pat. No. 8,992,594.

(60) Provisional application No. 61/286,820, filed on Dec. 16, 2009.

(51) Int. Cl.
| | |
|---|---|
| *A61L 27/50* | (2006.01) |
| *A61L 27/44* | (2006.01) |
| *A61B 17/11* | (2006.01) |
| *A61B 17/122* | (2006.01) |
| *A61F 2/06* | (2013.01) |
| *A61B 17/00* | (2006.01) |

(52) U.S. Cl.
CPC ............ *A61L 27/44* (2013.01); *A61L 27/507* (2013.01); *A61L 27/56* (2013.01); *A61B 2017/00252* (2013.01); *A61B 2017/00969* (2013.01); *A61B 2017/1107* (2013.01); *A61B 2017/1135* (2013.01); *A61F 2/064* (2013.01); *A61F 2210/0076* (2013.01)

(56) References Cited

U.S. PATENT DOCUMENTS

| | | |
|---|---|---|
| 6,187,038 B1 | 2/2001 | Sullivan et al. |
| 6,296,863 B1 | 10/2001 | Trogolo et al. |
| 6,891,077 B2 | 5/2005 | Rothwell et al. |
| 7,037,332 B2 | 5/2006 | Kutryk et al. |
| 7,452,374 B2 | 11/2008 | Hain et al. |
| 7,759,099 B2 | 7/2010 | Wolf et al. |
| 7,759,120 B2 | 7/2010 | Wolf et al. |
| 7,794,219 B2 | 9/2010 | Dubson et al. |
| 7,998,188 B2 | 8/2011 | Zilla et al. |
| 8,057,537 B2 | 11/2011 | Zilla et al. |
| 8,172,746 B2 | 5/2012 | Zilla et al. |
| 8,992,594 B2 | 3/2015 | Soletti et al. |
| 9,603,729 B2 | 3/2017 | Soletti et al. |
| 2002/0042128 A1 | 4/2002 | Bowlin et al. |
| 2002/0049495 A1 | 4/2002 | Kutryk et al. |
| 2002/0120348 A1 | 8/2002 | Melican et al. |
| 2003/0236567 A1 | 12/2003 | Elliot et al. |
| 2004/0058887 A1 | 3/2004 | Bowlin et al. |
| 2004/0094873 A1 | 5/2004 | Dubson et al. |
| 2004/0146546 A1 | 7/2004 | Gravett et al. |
| 2004/0215337 A1 | 10/2004 | Hain et al. |
| 2004/0219185 A1 | 11/2004 | Ringeisen |
| 2005/0203636 A1 | 9/2005 | McFetridge |
| 2006/0085063 A1 | 4/2006 | Shastri et al. |
| 2006/0204441 A1 | 9/2006 | Atala et al. |
| 2006/0240061 A1 | 10/2006 | Atala et al. |
| 2007/0173917 A1 | 7/2007 | Hayashi et al. |
| 2007/0237973 A1 | 10/2007 | Purdy et al. |
| 2007/0239267 A1 | 10/2007 | Hendriks et al. |
| 2007/0293932 A1 | 12/2007 | Zilla et al. |
| 2008/0208323 A1 | 8/2008 | El-Kurdi et al. |
| 2009/0012607 A1 | 1/2009 | Kim et al. |
| 2009/0036969 A1 | 2/2009 | Fitzpatrick et al. |
| 2010/0160718 A1 | 6/2010 | Villafana et al. |
| 2010/0280598 A1 | 11/2010 | Fox |
| 2012/0116495 A1 | 5/2012 | Zilla et al. |
| 2012/0271405 A1 | 10/2012 | Soletti et al. |
| 2012/0330437 A1 | 12/2012 | El-Kurdi et al. |
| 2015/0202063 A1 | 7/2015 | Soletti et al. |

FOREIGN PATENT DOCUMENTS

| | | |
|---|---|---|
| WO | WO-2004028583 A2 | 4/2004 |
| WO | WO-2004096095 A2 | 11/2004 |
| WO | WO-2010042721 A1 | 4/2010 |

OTHER PUBLICATIONS

Ben-Gal, et al. Expandable external support device to improve saphenous vein graft patency after cabg. J Cardiothorac Surg 2013;8:122.

Castronuovo, J. The sequence of gene expression in cultured human saphenous vein after injury. (2002) J. Vasc. Surg. 35, 146-151.

Chakrabarty, S. Fibrin solubilizing properties of certain anionic and cationic detergents. Thrombosis research 55.4 (1989): 511-519.

Courtney, et al. Design and anlysis of tissue engineering scaffolds that mimic soft tissue mechanical anisotropy. Biomaterials. 2006, 27: 3631-3638.

Deitzel, et al. Controlled deposition of electrospun poly(ethylene oxide) fibers. Polymer. 2001, 42: 8163-8170.

Deitzel, et al. The effect of processing variable on the morphology of electrospun nanofibers and textiles. Polymer 42 (2001): 261-272.

Ducasse, et al. Interposition vein cuff and intimal hyperplasia: An experimental study. Eur J Vasc Endovasc Surg. 2004;27(6): 617-21.

European search report and search opinion dated Oct. 23, 2015 for EP Application No. 10842584.4.

Fingerle. Intimal lesion formation in rat carotid arteries after endothelial denudation in absence of medial injury. (1990) Arteriosclerosis, 10, 1082-1087.

Grote, et al. Mechanical stretch enhances mRNA expression and proenzyme release of matrix metalloproteinase-2 (MMP-2) via nad(p)h oxidase-derived reactive oxygen species. Circulation Research. 2003;92(11): 80-6.

Hermans, et al. Fibrin: structure and interactions. Seminars in thrombosis and hemostasis. vol. 8. No. 1. 1982.

International search report and written opinion dated Sep. 23, 2011 for PCT Application No. US2010/060667.

Izzat, et al. Influence of External Stent Size on Early Medial and Neointimal Thickening in a Pig Model of Saphenous Vein Bypass Crafting, Circulation, 94(7):1741-1745, 1996.

Janowski-Bell, et al. Histology of Blood Vessels—www2.victoriacollege.edu/dept/bio/Belltutorials/Histology%20Tutorial/Blood%20Vessels/Histology_of_Blood_Vessels.html.

Jeremy, et al. A Bioabsorbable (Polyglactin), Nonrestrictive, External Sheath Inhibits Porcine Saphenous Vein Graft Thickening, Journal of Thoracic and Cardiovascular Surgery, 127(6):1766-1772, Jun. 2004.

Kohler, et al. Inhibition of neointimal hyperplasia in a sheep model of dialysis access failure with the bioabsorbable vascular wrap paclitaxel-eluting mesh. J Vasc Surg. 2007;45(5): 1029-1037; discussion 1037-8.

Kohler, et al. The Effect of Rigid External Support on Vein Graft Adaptation to the Arterial Circulation, J.. Vasc. Surg., 9(2):277-285, 1989.

Levorson, et al. Fabrication and characterization of multiscale electrospun scaffolds for cartilage regeneration. Biomed Mater 2013;8:014103. doi:10.1088/1748-6041/8/1/014103.

Linder, V. Mouse model of arterial injury. (1993) Circ. Res., 73, 792-796.

Manchio, J. Disruption of graft endothelium correlates with early failure after off-pump coronary artery bypass surgery. (2005) Ann. Thor. Surg. 79, 1991-1998.

McManus, et al. Electrospun fibrinogen: feasibility as a tissue engineering scaffold in a rat cell culture model. Journal of Biomedical Materials Research Part A 81.2 (2007): 299-309.

McManus, et al. Mechanical properties of electrospun fibrinogen structures. Acta Biomaterialia 2.1 (2006): 19-28.

Mehta, et al. External Stenting Reduces Long-term Medial and Neointimal Thickening and Platelet Derived Growth Factor Expression in a Pig Model of Arteriovenous Bypass Grafting, Nature Medicine, 4(2):235-239, Feb. 1998.

Moritz, et al. A Method for Constricting Large Veins for use in Arterial Vascular Reconstruction, Artificial Organs, 14(5):394-398, 1990.

Morton, et al. Electrospun fibrin nanofibers for the use in tissue engineering. Modification of fibrin to improve applications in regenerative medicine (2010): 81.

(56) References Cited

OTHER PUBLICATIONS

Mosesson, M. W. Fibrinogen and fibrin structure and functions. Journal of Thrombosis and Haemostasis 3.8 (2005): 1894-1904.
Notice of allowance dated Jan. 20, 2015 for U.S. Appl. No. 13/515,996.
Notice of allowance dated Aug. 18, 2014 for U.S. Appl. No. 13/515,996.
Notice of allowance dated Sep. 12, 2014 for U.S. Appl. No. 13/515,996.
Notice of allowance dated Dec. 29, 2014 for U.S. Appl. No. 13/515,996.
Office action dated Feb. 10, 2016 for U.S. Appl. No. 14/586,419.
Office action dated Mar. 11, 2014 for U.S. Appl. No. 13/515,996.
Office Action dated Jun. 24, 2016 for U.S. Appl. No. 14/586,419.
Office action dated Sep. 27, 2013 for U.S. Appl. No. 13/515,996.
Parsonnet, et al. New stent for support of veins in arterial grafts. Arch Surg. 1963;87: 696-702.
Perumcherry, et al. A Novel Method for the Fabrication of Fibrin-Based Electrospun Nanofibrous Scaffold for Tissue-Engineering Applications. Tissue Engineering Part C: Methods 17.11 (2011): 1121-1130.
Ramos, et al. Histologic fate and endothelial changes of distended and nondistended vein grafts. Ann Surg. 1976;183(3): 205-28.
Reneker, et al. Electrospinning of Nanofibers from Polymer Solutions and Melts. Adv Appl Mech 2007;41. doi:10.1016/S0065-2156(07)41002-X.
Sell, et al. Cross-linking methods of electrospun fibrinogen scaffolds for tissue engineering applications. Biomedical Materials 3.4 (2008): 045001.
Sepehipour, A. Does a 'no-touch' technique result in better vein patency? (2011) Interact Cardiovasc Thorac Surg., 13, 626-630.
Sreerekha, et al. Fabrication of fibrin based electrospun multiscale composite scaffold for tissue engineering applications. Journal of biomedical nanotechnology 9.5 (2013): 790-800.
Stankus, et al. Fabrication of biodegradable elastomeric scaffolds with sub-micron morphologies. J Biomed Mater Res A. 2004;70(4): 603-14.
Stankus, et al. Microintegrating smooth muscle cells into a biodegradable, elastomeric fiber matrix. Biomaterials. 2006;27(5): 735-44.
Stitzel, et al. Controlled fabrication of a biological vascular substitute. Biomaterials. 2006, 27: 1088-1094.
Stooker, et al. Perivenous Application of Fibrin Glue Reduces Early Injury to the Human Saphenous Vein Graft Wall in an Ex Vivo Model, European Journal of Cardio-thoracic Surgery, 21(2):212-217, 2002.
Tai, et al. Compliance properties of conduits used in vascular reconstruction. Br J Surg. 2000;87(11): 1516-24.
Traver, et al. New Generation Tissue Sealants and Hemostatic Agents: Innovative Urologic Applications. Reviews in Urology. 2006, 8: 104-111.
Vijayan, et al. External Supports and the Prevention of Neointima Formation in Vein Grafts, European Journal Vascular Endovascular Surg., 24(1):13-22, 2002.
Vijayan, et al. Long-term Reduction of Medial and Intimal Thickening in Porcine Saphenous Vein Grafts with a Polyglactin Biodegradable External Sheath, Journal Vascular Surgery, 40(5):1011-1019, 2004.
Wan, et al. Differential, time-dependent effects of perivenous application of fibrin glue on medial thickening in porcine saphenous vein grafts. European Journal of Cardio-thoracic Surgery, 29, (2006): 742-747.
Weisel, et al. Computer modeling of fibrin polymerization kinetics correlated with electron microscope and turbidity observations: clot structure and assembly are kinetically controlled. Biophysical journal 63.1 (1992): 111.
Weisel, et al. Mechanisms of fibrin polymerization and clinical implications. Blood 121.10 (2013): 1712-1719.
Wnek, et al. Electrospinning of nanofiber fibrinogen structures. Nano Letters 3.2 (2003): 213-216.
Xu, et al. Electrospun Nanofiber Fabrication as Synthetic Extracellular Matrix and Its Potential for Vascular Tissue Engineering. Tissue Engineering, vol. 10, No. 7/8, 2004.
Yu, et al. Electrospinning, Encyclopedia of Polymer Science & Technology (2008) 1-20.
Zilla, et al. Constrictive external nitinol meshes inhibit vein graft intimal hyperplasia in nonhuman primates. The Journal of Thoracic and Cardiovascular Surgery 2008;136:717-725.
Zilla, et al. Utilization of shape memory in external vein-graft meshes allows extreme diameter constriction for suppressing intimal hyperplasia: A non-human primate study. J Vasc Surg 2009;49:1532-42.
Australian Exam Report dated Feb. 19, 2015 for AU application No. 2010339931.
European Supplementary search report dated Nov. 10, 2015 for EP Application No. 10842584.4.

GRAFT DEVICES AND RELATED SYSTEMS AND METHODS

CROSS-REFERENCE TO RELATED APPLICATIONS

This application is a continuation of U.S. application Ser. No. 14/586,419 filed Dec. 30, 2014, which is a continuation application of U.S. application Ser. No. 13/515,996, filed on Jul. 11, 2012, now U.S. Pat. No. 8,992,594, issued on Mar. 31, 2015, which is a National Phase Application of International Application No. PCT/US2010/60667, filed Dec. 16, 2010, which claims benefit of and priority to Provisional Patent Application No. 61/286,820, filed Dec. 16, 2009. The disclosures of the above applications are incorporated herein by reference in their entireties.

TECHNICAL FIELD

This application relates generally to graft devices for a mammalian patient. In particular, this application relates to tubular graft devices comprising a tubular member and a fiber matrix.

BACKGROUND

Coronary artery disease, leading to myocardial infarction and ischemia, is currently the number one cause of morbidity and mortality worldwide. Current treatment alternatives consist of percutaneous transluminal angioplasty, stenting, and coronary artery bypass grafting (CABG). CABG can be carried out using either arterial or venous conduits and is the most effective and most widely used treatment to combat coronary arterial stenosis, with nearly 500,000 procedures being performed annually. In addition there are approximately 80,000 lower extremity bypass surgeries performed annually. The venous conduit used for bypass procedures is most frequently the autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed arterial vein grafts (AVGs) will die or require re-operation.

IH accounts for 20% to 40% of all AVG failures within the first 5 years. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH may be initiated by the abrupt exposure of the veins to the dynamic mechanical environment of the arterial circulation.

For these and other reasons, there is a need for devices and methods which provide enhanced AVGs and other grafts for mammalian patients. Desirably the devices will improve long term patency and minimize surgical and device complications.

SUMMARY

Developing a reliable means to prevent the early events of the IH process would contribute to improvements in the outcome of arterial bypass procedures. Therefore, provided herein is a method of mechanically conditioning and otherwise treating and/or modifying an arterial vein graft, or any tubular tissue (living cellular structure) or artificial graft, typically, but not exclusively, in autologous, allogeneic xenogeneic transplantation procedures. To this end, provided herein is a method of wrapping a tubular graft, including, without limitation, a vein, artery, urethra, intestine, esophagus, trachea, bronchi, ureter, duct and fallopian tube. The graft is wrapped with a fiber matrix, typically with a biodegradable (also referred to as bioerodible or bioresorbable) polymer about a circumference of the tubular tissue. In one non-limiting embodiment, the matrix is deposited onto tubular tissue by electrospinning. In one particular non-limiting embodiment, the tubular tissue is a vein, such as a saphenous vein, that is used, for instance, in an arterial bypass procedure, such as a coronary artery bypass procedure.

This new approach would have two potential applications. In the first non-limiting application, the matrix can be used as a peri-surgical tool for the modification of vein segments intended for use as an AVG. The modification of the vein or other tubular structure would be performed by treating the structure at bedside, immediately after removal from the body and just prior to grafting. In one non-limiting example, after the saphenous vein is harvested, and while the surgeon is exposing the surgical site, the polymer wrap would be electrospun onto the vein just prior to it being used for the bypass procedure.

According to a first aspect of the invention, a graft device for a mammalian patient is disclosed. The graft device includes a tubular member having a first end and a second end, a fiber matrix at least partially surrounding the tubular member, and at least one of a reinforced portion or an anastomic connector located on at least one of the first end or the second end. The reinforced portion and/or the anastomic connector provide strength/reinforce their respective end of the graft device, thereby allowing for an improved connection with the mammalian patient. In one embodiment, the reinforced portion is formed of a modification of the fiber matrix. That is, a portion of the fiber matrix has properties that are modified from a remaining portion of the matrix. The modified properties provide additional strength/reinforcement to the underlying tubular member. In an embodiment, the reinforced portion comprises a reinforcing element, such as a band positioned on the interior or exterior of at least one of the first or second end of the tubular member. In an embodiment, the graft includes both the reinforced portion and the anastomic connector.

According to a second aspect of the invention, a graft device comprising a tubular member and a surrounding fiber matrix is disclosed.

The above aspects can include one or more of the following features. The tubular member is typically a harvested vein segment, such as a harvested portion of a saphenous vein. The fiber matrix is typically a fiber mesh electrospun on the tubular member, such as in a sterile setting such as an operating room of a hospital. The graft device may be constructed according to one or more parameters listed in Table 1 here below. The graft device comprises or otherwise performs according to one or more parameters listed in Table 1 here below. The graft device may be customized to the patient, typically a human patient, based on one or more morphological or functional cues of the patient. Such clues include but are not limited to: vessel size such as vessel diameter, length and/or wall thickness, taper or other geometric property; size and location of vessel side branch ostium or antrum; patient age or sex; vessel elasticity or compliance; vessel vasculitis; vessel impedance; specific genetic factor or trait; and combinations of these.

In one embodiment, the tubular member is a patient harvested conduit such as a portion of a conduit selected from the group consisting of: a saphenous vein graft or other vein; an artery; the urethra; intestine; esophagus; ureter; trachea; bronchi; a duct; a fallopian tube; and combinations of these. In an alternative embodiment, the tubular member is an artificial conduit, such as a polytetrafluoroethylene (PTFE) conduit, such as a round or flat tube with a first end, a second end, and a lumen therethrough. In yet another alternative embodiment, the tubular member is a tissue engineered structure or organ. The tubular member may comprise one or more of: a biological based scaffold; a synthetic based scaffold; a structure seeded with adult differentiated cells or undifferentiated stem cells; a structure treated with synthetic, biological and/or biomimetic cues such as cues to enhance antithrombogenicity and/or enhance selective or non-selective cell repopulation; and combinations of these.

The graft device may have a fiber matrix with a designated permeability, such as a permeability based on a patient parameter. The fiber matrix may be constructed based on a parameter of the harvested vessel or other conduit (hereinafter "vessel"), such as a fiber matrix with a geometry customized to a harvested vessel. The fiber matrix internal diameter may be chosen to create a diameter smaller than the external diameter of the vein prior to harvesting. The graft device may be customized to the vessels in which it is to be fluidly connected (anastomosed), such as customization to the aorta and a diseased artery. The graft device may include additional advantages including but not limited to: atraumatic ends; easily customizable lengths; repeatability in creating a first graft device and a second graft device such a repeatability achieved in a machine controlled process; and ease of removability. The graft device may include one or more structural nodes in the fiber matrix. Nodes can be created in the creation of the fiber matrix, such as during an electrospin process, or by post processing such as a heating device which melts one fiber to another. In a typical embodiment, during the electrospin process, a first fiber and a second fiber have a contact point, the contact point melting together as the fiber matrix cools.

The fiber matrix has a thickness profile between its two ends. The thickness profile may be symmetric, such as symmetry about or midpoint (e.g., ends thicker than middle or middle thicker than the ends) or a relatively constant thickness from a first end to a second end. The thickness profile may be asymmetric, such as varying thickness based on the thickness or other property of the tubular member. Thickness variations may be relatively linear or non-linear increases or decreases (i.e., following continuous functions) or variations may consist of more abrupt step changes (i.e., following discrete functions), such as a step increase in each end used to reinforce the ends of the graft device.

In another embodiment, the fiber matrix is biodegradable or includes one or more biodegradable portions. Biodegradation rates are typically greater than two weeks, and biodegradation rate may vary across the length of the graft device, such as by the use of multiple materials in the fiber matrix or by varying the thickness of a homogeneous fiber matrix.

The fiber matrix may be anisotropic, such as when the radial stiffness of the fiber matrix is greater than the axial stiffness. The fiber matrix may have a length greater than the length of the tubular member, such that one or both ends of the fiber matrix extend beyond the associated end of the tubular member. This extending portion may be useful in fixating in one or more additional devices connected to the graft device, such as the fiber matrix overlapping an anastomotic connector.

The graft device has a first end and a second end, and these ends may be anastomosed to a source of blood and a diseased artery in a coronary heart bypass procedure. The first end is fluidly connected to a source of arterial blood such as the aorta, another artery proximate the patient's heart such as an internal mammary artery, or a previously placed bypass graft such as previously placed saphenous vein graft or graft device of the present invention. The second end is attached to a point distal to a diseased coronary artery, such as an artery on the left side or right side of the heart. In addition, a mid portion of the graft may be anastomosed to a second diseased coronary artery, in a side-to-side anastomosis, such as to create a serial grafting from a single source of arterial blood that results in a higher flow rate through portions of the graft device. More than two serial connections can be created. The graft device may be sized to maintain a minimum sheer stress of blood flow, typically between 2 and 30 dynes/cm$^2$, preferably between 12 and 20 dynes/cm$^2$. One or more graft device ends can be spatulated or otherwise cut or modified to improve the anastomosis. The cut or other modification may modify the tubular member, the fiber matrix, or both.

The fiber matrix may be sized to have a specific pore size distribution, porosity, and permeability. The fiber matrix may be configured to reduce leukocyte transmission by restricting permeability and/or reduce inflammation and/or intimal hyperplasia, such as with an average pore size less than 7 microns and/or a porosity between 50% and 95%.

The fiber matrix surrounds the tubular member, and may be configured to have relatively continuous contact with the outer diameter of the tubular member, or provide a small separation such as a separation configured to allow small radial expansions of the tubular member. In an alternative embodiment, one or more ends of the fiber matrix are flared radially outward, such as to allow additional expansion of the tubular member, such as might occur in the creation of an anastomosis or other manipulation of the ends of the graft device. The fiber matrix is preferably a restrictive fiber matrix, restricting expansion of the tubular member, such as when the tubular member is a saphenous vein segment and this segment is exposed to arterial pressure. The fiber matrix typically maintains radial expansion of a venous tubular member to a radial stretch less than or equal to 30%. The fiber matrix typically has a pore size between 10 and 1,000 microns, preferably between 100 and 500 microns. The fiber matrix typically has a porosity between 50% and 95%, typically 60% to 90%. The fiber matrix may be hydrophilic.

The graft device may have one or more ends reinforced, such as an end with a fiber matrix difference from a mid portion of the fiber matrix, the difference selected from the group consisting of: a thicker matrix, different or additional material in the matrix; material with a different biodegradation rate; and combinations of these. Alternatively or additionally, an end may include a reinforcing element, such as a band placed inside of the tubular member, between the tubular member and the fiber matrix, and outside of the fiber matrix. The reinforcing element may include one or more holes used in the anastomosis, and may be plastically deformable, resiliently biased, or both. The reinforcing element may biodegrade, such as at a similar rate to a biodegradable fiber matrix, or at a different rate.

In yet another embodiment, the graft device includes one or more anastomotic connectors. The anastomotic connector may include axial projections, such as axial projections that reside between the tubular member and the fiber matrix, or axial projections that are configured to be placed (e.g., by a surgeon during a bypass procedure) between the tubular member and the fiber matrix. Alternatively or additionally, axial projections may reside within the tubular member. The end of the graft device may be modified in one or more ways to assist in creating the anastomosis, such as modifications including one or more of: thicker fiber matrix; thinner fiber matrix; flared fiber matrix; hook and loop component at device end; adhesive surface; second fiber in fiber matrix; and a magnetic component at the device end. The anastomotic connector has a longitudinal axis and may have an end which is orthogonal to the longitudinal axis, or the end may be at an angle less that 90° to the longitudinal axis.

In yet another embodiment, the graft device includes an intermediate layer, such as a layer of fibrin glue, between the fiber matrix and the tubular member. The intermediate layer may be configured to provide one or more of the following functions: provide an adhesive layer between the tissue and the matrix, protect (e.g., mechanically and/or chemically) the tubular member during fiber deposition process; provide nutrients; provide an agent such as a drug; and provide a mechanically or geometrically useful intermediate layer (e.g., compressible, incompressible, elastic, viscoelastic, or viscous) between the tubular member and the fiber matrix to control vein mechanical properties (e.g., compliance), and/ or geometrical features (e.g., wall thickness).

In yet another embodiment, the graft device includes a band. The band, typically a reinforcing band at one or both ends, may extend beyond the end of the fiber matrix, the tubular member, or both. The band may be placed within the tubular member, between the tubular member and the fiber matrix, or outside of the fiber matrix. The band may biodegrade and may include at least a resiliently biased portion.

According to another aspect of the invention, a method of placing a graft device is disclosed. A graft device is selected as has been described in this application, and includes a tubular member and a surrounding fiber matrix. A first anastomotic connection is created between a first end of the graft device and a first body space. A second anastomotic connection is created between a second end of the graft device and a second body space. The first body space is typically a source of arterial blood such as the aorta. The second body space is typically an artery, such as a diseased coronary artery distal to a blockage in that artery. The method may include harvesting a patient conduit, such as a blood vessel such as a saphenous vein graft. Ligation of side branches may be needed to prepare the graft for a fiber matrix deposition process such as a fiber matrix applied with an electrospinning process. In one non-limiting embodiment, non-metal ligation devices such as suture or plastic clips are used to avoid adversely impacting the electrospinning process.

In one embodiment, a graft device is configured based on one or more patient vessel or other patient condition. Multiple graft devices may be configured and connected to two or more body spaces of the patient. Fluid connections are made between a body space such as the aorta in an end-to-side anastomosis, and a coronary artery in a side-to-side anastomosis (e.g., at a mid portion of the graft device) and/or in an end-to-side anastomosis (e.g., at the second end of the graft device). One or both device ends may be modified prior to or during the anastomosis procedure such as in a spatulation or other procedure cutting the end of the device, or a procedure in which the tubular member members are stretched (with or without stretching the fiber matrix). Stretching of the tubular member ends may occur with or without intent during the creation of the anastomosis. One or both device ends may be cut prior to anastomosis creation, such as a cut to the tubular member and/or fiber matrix at a right angle or at an oblique angle to the longitudinal axis of the device.

In another embodiment, the graft device includes a preattached or attachable anastomotic connector. The anastomotic connector may include axial projections that reside within the tubular member, between the tubular member and the fiber matrix, and/or outside the fiber matrix. The graft device may include a fiber matrix with modified ends, such as ends that include one or more of: thicker fiber matrix; thinner fiber matrix; flared fiber matrix; hook and loop component at device end; adhesive surface; second fiber in fiber matrix; and a magnetic component at device end. The modified ends may be included to further secure the anastomosis such as suture or clips that pass through a reinforced fiber matrix end. The modified ends may be included to simplify the attachment procedure, such as device ends which include adhesive or a magnetic component configured to aid in positioning and maintaining position of the device end during the creation of the anastomosis.

The method may include removing the fiber matrix from the tubular member, such as when an issue has been identified. The method may further include application of a second fiber matrix, or implantation of the tubular member without a surrounding fiber matrix. The method may include applying a fiber matrix to a tubular member that is longer than needed, subsequent to which the device is cut to length, such as at a right angle or oblique angle to the device longitudinal axis.

BRIEF DESCRIPTION OF THE DRAWINGS

The accompanying drawings, which are incorporated in and constitute a part of this specification, illustrate various embodiments of the present invention, and together with the description, serve to explain the principles of the invention. In the drawings.

DETAILED DESCRIPTION OF THE DRAWINGS

Figure 1:
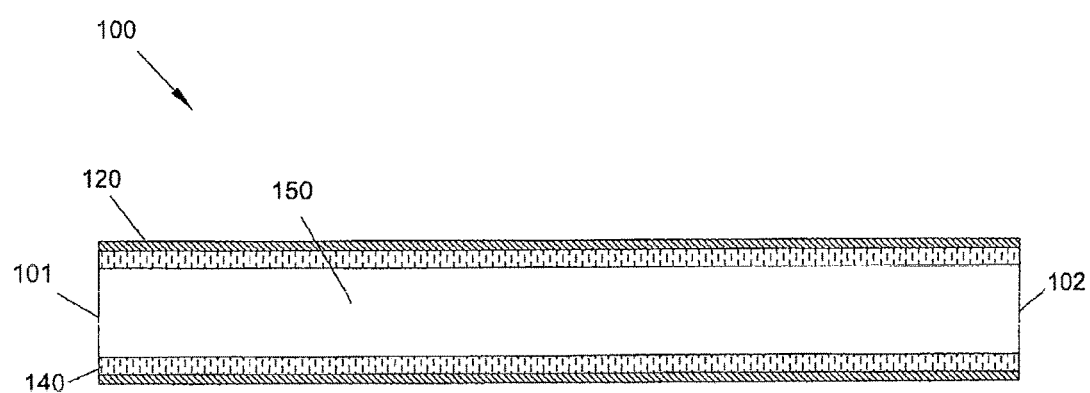
FIG. 1 illustrates a side sectional view of a graft device for a mammalian patient including a tubular member and a surrounding fiber matrix, consistent with the current invention.

Reference will now be made in detail to the present embodiments of the invention, examples of which are illustrated in the accompanying drawings. Wherever possible, the same reference numbers will be used throughout the drawings to refer to the same or like parts.

Provided herein is a method of mechanically conditioning vessel to vessel graft, or any tissue or artificial conduit or other structure, typically, but not exclusively, in autologous, allogeneic xenogeneic transplantation procedures. To this end, provided herein is a method of wrapping or otherwise covering tissue, including, without limitation, a vein; artery; urethra; intestine; esophagus; ureter; trachea; bronchi; duct; fallopian tube; and combinations of these (meaning the entire structure or a portion of those tissues). Alternatively, an artificial, non-tissue, structure may be covered. The structure is wrapped or coated with a fiber matrix of a biodegradable polymer. As described herein, a "fiber" comprises an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning).

The matrix typically is substantially or essentially contiguous about a circumference of a tubular tissue, meaning that the matrix forms a continuous, supportive ring on a surface and about a circumference of a portion, but not necessarily over the entire surface (e.g., length) of the tubular tissue. The matrix may be "restrictive," meaning that the matrix is in substantial contact with the outer surface of the tubular tissue, or is narrowly spaced and proximate to the outer surface of the tubular tissue, and reinforces, restricts, hinders and/or prevents substantial circumferential expansion of the tubular tissue when used as a bypass graft or otherwise radially expanded. The degree of restriction by the matrix typically is such that when exposed to internal pressure, such as typical arterial pressures, the tubular tissue is prevented from distending to the extent that would occur without such restriction. The matrix typically comprises a durable material but may also be biodegradable, such as when the restrictive nature of the matrix may decline over time as the matrix biodegrades.

In one non-limiting embodiment, the matrix is deposited onto a tubular tissue, such as a tubular anatomical structure or organ, by an electrospinning process. In another particular non-limiting embodiment, the anatomical structure is a vein, such as a saphenous vein, that is used, for instance, in an arterial bypass procedure, such as a coronary artery bypass procedure. In another non-limiting embodiment, the matrix is deposited onto a tissue-engineered tubular anatomical structure or organ, comprised of a scaffold (biological- or synthetic-based) material that is either seeded with adult differentiated cells or undifferentiated stem cells, or unseeded, or a scaffold treated with synthetic, biological, or biomimetic cues (e.g., to enhance antithrombogenicity, to reduce inflammation, and/or immune response, to avoid cell adhesion and growth, to foster selective or non-selective cell repopulation once implanted in vivo). In another non-limiting embodiment, the matrix is deposited onto an artificial material, such as an artificial graft such as a polytetrafluoroethylene (PTFE) graft.

Although any useful method of depositing fine fibers onto a surface could be employed, electrospinning is a useful method of depositing substantially uniform fibers onto a surface, particularly the outside of a tubular structure. Electrospinning permits fabrication of graft devices that mimic certain morphological and mechanical aspects, especially the fibrous nature of a native extracellular matrix (ECM). The ECM is composed of fibers, pores, and other surface features at the sub-micron to nanometer size scale. Such features directly impact physiologic response to biological-based or synthetic-based materials such as by impacting attachment, cell migration and orientation, proliferation, viability, inflammation reaction, and gene expression. Electrospinning also permits fabrication of oriented fibers to result in devices with inherent anisotropy. These aligned matrices can result in directional properties, for example greater stiffness in the radial versus axial direction of the underlying tubular tissue.

Generally, the process of electrospinning involves placing a polymer-containing fluid (e.g. a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a conductor (typically a collector screen or rotating mandrel) positioned proximate to a target. During electrospinning, the polymer-containing fluid is charged by the application of high voltage to the solution or orifice (e.g., multiple kV) and then infused through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target. Optionally, a focusing ring with an applied bias can be used to direct the trajectory of the charged jet of polymer-containing fluid. Additionally, a number of other techniques can be used to control the polymer jet trajectory onto the target including but not limiting to a Faraday cage surrounding the electrospinning field, a selective electrical insulation of nozzle and/or target, and a selective local application of the electrical field. As the charged jet of fluid travels towards the biased target, it undergoes a complicated whipping and bending motion. If the fluid is a polymer solution or suspension, the solvent might undergo variable levels of evaporation during mid-flight (depending of the volatility of the solvent, and the process parameters), leaving behind a polymer fiber on the biased target with variable levels of residual solvent. Amounts of residual solvent upon the end of fiber travel usually allow for solvent-bonding of the deposited fibers and creation of structural nodes in the matrix. If the fluid is a polymer melt, the molten polymer might undergo variable levels of cooling and solidification in mid-flight and is collected as a polymer fiber on the biased target. Residual temperature of the fibers might allow for thermal-bonding of the fibers and creation of structural nodes in the matrix. As the polymer fibers accumulate on the biased target, a non-woven, porous mesh (matrix) is formed on the biased target.

The properties of the electrospun elastomeric matrices can be tailored by varying the electrospinning conditions and/or other process parameters. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice, such as to create a matrix that is thicker at one location than another. In certain embodiments, the biased emitter and target are moved in a relative fashion. The relative motion between emitter and target can be periodic or not, or can follow any relative body motions including but not limiting to translational, rotational, elicoidal, planar, roto-translational, and spherical motions such as that the resulting net fiber orientation is controlled and aligned along preferential directions. When this is the case, the resulting non-woven mesh may have a higher resistance to strain in the direction parallel to the fibers, compared to the direction perpendicular to the fibers (anisotropic). In other embodiments, the biased target is moved randomly relative to the orifice, so that the resistance to strain in the plane of the non-woven mesh is isotropic. The target can also be an object surrounding a rotating mandrel. In this case, the properties of the non-woven mesh may be changed by varying the speed of rotation. The properties of the electrospun elastomeric matrix may also be varied by changing the magnitude of the voltages applied to the electrospinning system or the chemical (e.g., chemical composition, density, etc.) or physical (e.g., temperature, viscosity, surface tension, conductivity, etc.) characteristics of the polymer solution used.

Electrospinning may be performed using two or more nozzles, wherein each nozzle may be a source of a different polymer solution. The nozzles may be biased with different biases or the same bias in order to tailor the physical and chemical properties of the resulting non-woven polymeric mesh. Additionally, many different targets may be used.

When the electrospinning is to be performed using a polymer suspension, the concentration of the polymeric component in the suspension can also be varied to modify the physical properties of the matrix. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower concentration solutions have a lower viscosity, leading to faster flow through the orifice to produce thinner fibers. One skilled in the art can adjust polymer solution chemical and physical properties and process parameters to obtain fibers of desired characteristics, including fibers whose characteristics change along the length or width of the target.

In use, a mandrel, for example a rod that is formed of a conductive material such as stainless steel, can be placed inside a tubular conduit, such as a vein, and polymer fibers are deposited about the circumference of at least a portion of the tissue by rotation of the mandrel. Thickness of the matrix can be controlled by either adjusting the chemical or physical properties of the polymer solution to be deposited and/or adjusting duration of the electrospinning. Use of more viscous polymer composition may result in thicker fibers, requiring less time to deposit a matrix of a desired thickness. Use of a less viscous polymer composition may result in thinner fibers, requiring increased deposition time to deposit a matrix of a desired thickness. The thickness of the matrix and fibers within the matrix affects the speed of biodegradation of the matrix. Biodegradation may also be varied by altering the surface finish or porosity of the fibers, which can be altered by using solvents or diluents that evaporate at varying rates or also be adding purifiers to the solution, such as unmiscible fluids, emulsified particles or undissolved solids that can be later dissolved, thereby creating pores. These parameters are optimized, depending on the end-use of the matrix, to achieve a desired or optimal physiological effect. Thickness can be varied along the length of a target in a regular or irregular fashion, such as in creating a target that is thicker at one or both ends, in the center or as with a location-dependent symmetrical or asymmetrical thickness. In another particular embodiment, the thickness is varied by moving an electrospinning nozzle back in forth slowly near a specific circumferential location, thereby depositing more material proximate to that area. In yet another particular embodiment, fiber matrix thickness is determined by the thickness of the tubular member, such as when the fiber matrix is thicker at a circumferential portion of the tubular member that is thinner than other circumferential portions of the tubular member.

A biodegradation rate of the polymer matrix may be manipulated, optimized or otherwise adjusted so that the matrix degrades over a useful time period. For instance, in the case of a coronary artery bypass, it is desirable that the matrix dissolves over 12 hours or more, typically two weeks or more, so as to prevent substantial sudden stress on the graft. The polymer degrades over a desired period of time so that the mechanical support offered by the polymer matrix is gradually reduced over that period and the vein would be exposed to gradually increasing levels of circumferential wall stress (CWS).

This new approach would have two potential applications. In the first non-limiting application, the matrix can be used as a peri-surgical tool for the modification of vein segments intended for use as an arterial vein graft (AVG). The modification of a vein or other tubular tissue or anatomical structure may be performed at bedside, immediately after removal from the body and just prior to grafting, for example and without limitation, during arterial bypass surgery. In one non-limiting example, after the saphenous vein is harvested, and while the surgeon is exposing the surgical (graft) site, the polymer wrap would be electrospun onto the vein just prior to it being used for the bypass procedure.

In a second non-limiting embodiment, the polymer matrix can be used as a vehicle for the delivery of support to AVGs. While modification of the mechanical environment of a vein graft over time could itself improve AVG patency, delivery of active agents and biological support to AVGs may prove desirable in many instances. By tuning an electrospun polymer wrap, in which active agents and/or biological materials are incorporated (e.g., biochemicals, drugs, genes, growth factors, cytokines, and/or cells), to degrade at a desired rate, the rate of delivery of these support modalities could be controlled.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

The polymer or polymers typically will be selected so that it degrades in situ over a time period to optimize mechanical conditioning of the tissue. Non-limiting examples of useful in situ degradation rates include between 2 weeks and 1 year, and increments of 1, 2, 4, 8, 12, and, 24 weeks therebetween. Biodegradation may occur at different rates along different circumferential and/or axial portions of the matrix.

The biodegradable polymers useful herein also can be elastomeric. Generally, any elastomeric polymer that has properties similar to that of the soft tissue to be replaced or repaired as appropriate. For example, in certain embodiments, the polymers used to make the wrap are highly distensible. Non-limiting examples of suitable polymers include those that have a breaking strain of from 100% to 1700%, more preferably between 200% and 800%, and even more preferably between 200% and 400%. Further, it is often useful to select polymers with tensile strengths between 10 kPa-30 MPa, more preferably between 5-25 MPa, and even more preferably between 8 and 20 MPa. In certain embodiments, the elastic modulus calculated for physiologic levels of strain is between 10 kPa to 100 MPa, more preferably between 500 kPa and 10 MPa, and even more preferably between 0.8 MPa and 5 MPa.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

As used herein, the descriptor "tubular" does not refer specifically to a geometrically perfect tube having a constant diameter and a circular cross-section. It also embraces tissues having non-circular and varying cross sections, and can have a variable diameter, and thus any shape having a contiguous wall surrounding a lumen (that is, they are hollow), and two openings into the lumen such that a liquid, solid or gas can travel from one opening to the other. As indicated herein, specific non-limiting, but illustrative examples of tubular tissues include arterial, urethral, intestinal, esophageal, ureter, tracheal, bronchial, ductal, and fallopian tube tissue. In a preferred embodiment, tubular tissue includes a harvested saphenous vein graft. Alternatively, the tubular member may be artificial (non-tissue), such as a polytetrafluoroethylene (PTFE) tube or patch. The tubular member may also be a tissue engineered vascular graft, comprised of a matrix (biological- or synthetic-based) material that is either seeded with adult differentiated cells or undifferentiated stem cells, or unseeded, or a matrix treated with synthetic, biological, or biomimetic cues to enhance antithrombogenicity or selective or non-selective cell repopulation once implanted in vivo.

Also provided herein is a device for a mammalian patient. The device has improved anastomic connection capabilities. The device includes a tubular member having a first end and a second end, a fiber matrix at least partially surrounding the tubular member, and at least one of a reinforced portion or an anastomic connector located on at least one of the first end or the second end of the tubular member. In an embodiment, the reinforced portion comprises an area or portion of the fiber matrix, which includes a modification of matrix properties as compared to a remaining portion of the fiber matrix. In another embodiment, the reinforced portion comprises a reinforcing element, such as, for example a band. The reinforced portion provides additional strength to the ends of the tubular member to allow for an improved connection (e.g., anastomic connection) with the mammalian patient. The anastomic connector provides a mechanically secure connection with the patient and can also reinforce the end of the tubular member of the graft. In embodiments in accordance with this aspect of the invention, the graft can include both the reinforced portion and the anastomic connector.

Referring now to FIG. 1, a side sectional view of a graft device of the present invention is illustrated. Graft device 100 includes tubular member 140, circumferentially surrounded by fiber matrix 120. Graft device 100 includes a first end 101, and a second end 102, and is preferably configured to be placed between a first body location and a second body location of a patient. Graft device 100 includes lumen 150 from first end 101 to second end 102, such as to carry blood when graft device 100 is connected between the two blood vessels. Fiber matrix 120 is preferably applied using an electrospinning process, as has been described in detail hereabove. The electrospinning process may be performed in an operating room, such as when tubular member 140 is a harvested saphenous vein graft to be anastomosed between the aorta and a location on a diseased coronary artery distal to an occlusion. End to side anastomotic connections are typically used to attach device 100 to the aorta and disease artery. Alternatively, a side to side anastomosis can be used, such as to attach an end of device 100 to multiple arteries in a serial fashion. Alternate sources of arterial blood can be attached to device 100, such as an internal mammary artery (IMA), or another graft, such as another device 100, typically with an end to side anastomosis.

Fiber matrix 120 may be processed in a way specific to a patient morphological or functional parameter. These parameters may be selected from the group consisting of: vessel size such as diameter, length, and/or wall thickness; taper or other geometric property of a harvested vessel or vessel intended for anastomotic attachment; size and location of one or more side branch ostium or antrum within the harvested vessel; patient age or sex; vessel elasticity or compliance; vessel vasculitis; vessel impedance; specific genetic factor or trait; and combinations of these. Tubular conduit 140 is preferably free of any metal or magnetic material (in embodiments in which the matrix is deposited via electrospinning), such as metal clips used to ligate a side branch of a harvested saphenous vein.

Fiber matrix 120 when used for arterial vein grafts may be processed in a way to achieve a certain blood flow rate or shear stress within the treated arterial vein graft. In a typical configuration, shear stress within the arterial vein graft is between 2-30 dynes/cm$^2$, preferably 12-20 dynes/cm$^2$ is achieved. Fiber matrix 120 may be processed in a way to control the oxygen, nutrients, or cellular permeabilities between the extravascular tissues and the abluminal surface of the treated hollow tissue. Such permeabilities depend on the polymer chemical and physical properties, the pore size distribution, porosity, and pore interconnectivity. In a non-limiting example, cellular permeability can be selectively restricted to reduce leukocyte infiltration across the deposited fiber matrix with pore sizes smaller than 7 microns and porosities between 50% and 95%. Generally, oxygen, nutrients, and cellular (e.g., endothelial cells, endothelial progenitor cells, etc.) permeability are required to improve the treated hollow tissue in vivo remodeling and healing process. To this end the pore size range is typically between 10 and 1000 microns, preferably between 200 and 500 microns, and the porosity range typically between 50% and 95%, preferably between 60% and 90%. The pores preferably are highly interconnected so that a relatively straight path along the radial direction of the fiber matrix can be traced from most of the pores across the total thickness of the matrix. The polymer is typically hydrophilic.

Radial constriction of saphenous vein grafts has been achieved with stent devices placed over the vein prior to anastomosing the graft to the targeted vessels. The devices of the present invention provide numerous advantages over the stent approaches. The devices of the present invention can have one or more parameters easily customized to a parameter of the harvested vessel and/or another patient parameter. The fiber matrix can be customized to a harvested vessel parameter such as geometry, such as to reduce the vein internal diameter to produce desired flow characteristics. The fiber matrix can be customized to a target vessel parameter (e.g., the aorta and diseased artery), such as to be compatible with vessel sizes and/or locations. The fiber matrix can be modified to simplify or otherwise improve the anastomotic connections, such as to be reinforced in the portion of the device that is anastomosed (e.g., portion where suture and/or clips pass through) and/or to protrude beyond the length of the tubular member and overlap other members connected to the graft device. The devices of the present invention can be made to a wide array of lengths during the procedure, without the need for cutting, such as the cutting of a stent device, which might create dangerously sharp edges. The fiber matrix is applied to the tubular member in a controlled manner, repeatable manner, by an apparatus such as an electrospinning instrument. The ends of the fiber matrix are atraumatic, avoiding tissue damage at the anastomotic sites. In addition, the fiber matrix of the present invention is easily and atraumatically removable, such as to apply another fiber matrix. Stent devices are applied manually by the clinician, require significant manipulation, which could cause iatrogenic damage, have issues with reproducibility and accuracy limitations, and are difficult to reposition or remove, particularly without damaging the harvested vessel.

In a preferred embodiment, device 100 performs or is produced by one or more parameters listed in Table 1 immediately here below:

TABLE 1

| Category | Typical and Preferred Settings |
| --- | --- |
| Fiber Matrix Applicable Polymers | Typical: PEUU (2-30%); PCL (5-35%); PCL:PGA/PLLA (5-35% - from 80:20 to 50:50); PCL:PLLA (5-35% - from 80:20 to 50:50); PVDF; PVDF-HFP; Silk; Fibroin Preferred: PEUU (5-10%); PCL (5-15%); PCL:PGA (5-15% - 50:50); PCL:PLLA (5-15% - 50:50); PVDF; PVDF-HFP; Silk; Fibroin |
| Fiber Matrix Process Solvents (e.g., electrospin solvents) | Typical: HFIP; DMSO; Chloroform; THF; DMF; Dichloromethane; DMAC, Dioxane; Toluene; Water; Acetone; Methanol; Propanol; Ethanol; Lithium Bromide; Aqueous Solutions (alkaline/acidic) Preferred: HFIP; DMF; THF; DMSO; Water More Preferred: HFIP; Water |
| Fiber Matrix Thickness | Typical: 50-1000 µm Preferred: 50-200 µm More Preferred: 50-150 µm |
| Fiber Matrix O$_2$ Permeability | Typical $10^{-10}$ to $10^{-6}$ (cm$^2$ mL O$_2$)/(s mL mmHg) |
| Fiber Matrix Porosity | Typical 50%-95% Preferred 85%-90% |

TABLE 1-continued

| Category | Typical and Preferred Settings |
| --- | --- |
| Fiber Matrix average Pore Size | Typical<br>0.001-2.0 mm<br>Preferred<br>0.10-1.0 mm<br>Also Preferred<br>0.005-0.020 mm |
| Fiber Matrix Compliance (measured in arterial-like conditions 70-110 mmHg) | Typical<br>2-100 × $10^{-4}$ mmHg$^{-1}$<br>Preferred (arterial blood applications)<br>2-15 × $10^{-4}$ mmHg$^{-1}$ |
| Fiber Matrix Anastomotic Retention Force (e.g., suture retention) | Typical<br>1-10 N |
| Fiber Matrix Circumferential Elastic Modulus (Static Elastic Modulus E) | Typical<br>0.5-2.0 MPa<br>Preferred<br>0.8-2.0 MPa |
| Fiber Matrix Viscoelasticity (Dynamic Elastic Modulus G) | Typical<br>between 1-fold and 2-fold E |
| Fiber Matrix Degradation Kinetics (in vivo complete resorption) | Typical<br>greater than 2 weeks<br>Preferred<br>linear reduction over 3-6 months |
| Fiber Matrix Hardness | Typical<br>polymer Brinnell Scale between 5 and 40 |
| Fiber Matrix Roughness | Typical<br>2-50 µm |

Referring now to FIGS. 1a, 1b, 1c and 1d microscopic views of a fiber matrix of the present invention is illustrated. Scanning electron microscope images of an electrospun fiber matrix, matrix 120, has been made using 8% (w/v) polycaprolactone solution in hexafluoroisopropanol (HFIP).

Figure 1A:
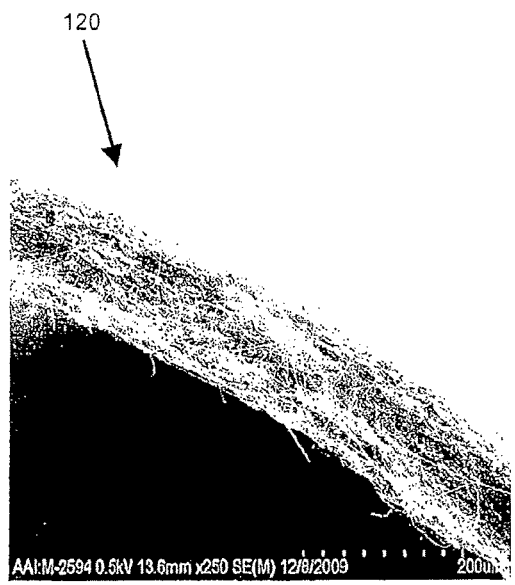
FIG. 1a through 1d illustrate microscopic photos of a fiber matrix, consistent with the current invention.
Figure 1B:
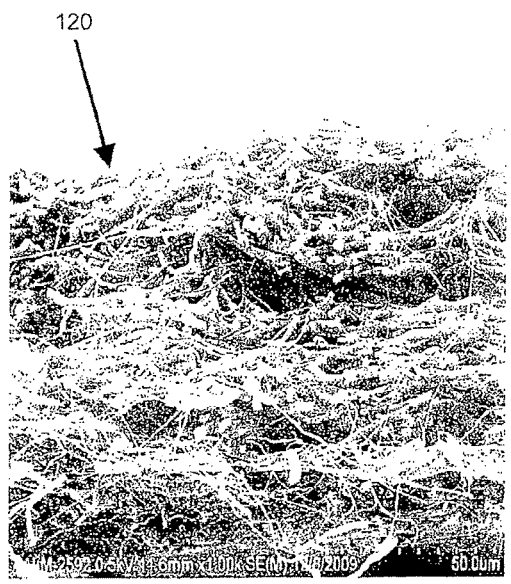
Figure 1C:
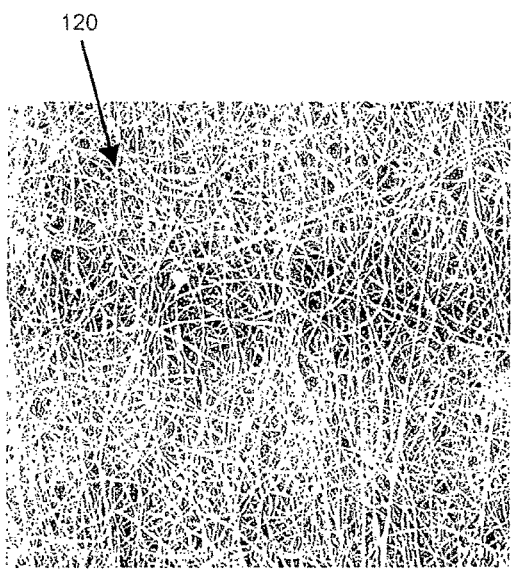
Figure 1D:
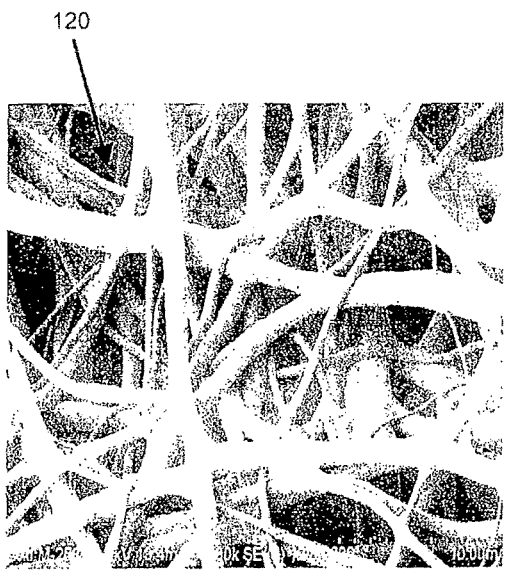

FIG. 1a illustrates a cross-sectional view obtained by cold fracture of matrix 120 in liquid nitrogen. Note the uniform thickness of about 100 microns consistent along the longitudinal and the circumferential directions of the matrix 120. FIG. 1b illustrates a close-up of cross sectional view. FIG. 1c illustrates an abluminal surface view of matrix 120. Note the high porosity of the matrix and the randomly oriented fiber direction (isotropy). FIG. 1d illustrates a close-up of matrix 120 for surface evaluation. Note the high porosity and wide distribution of fiber sizes ranging from 0.5 micron to 2 microns.

Figure 1E:
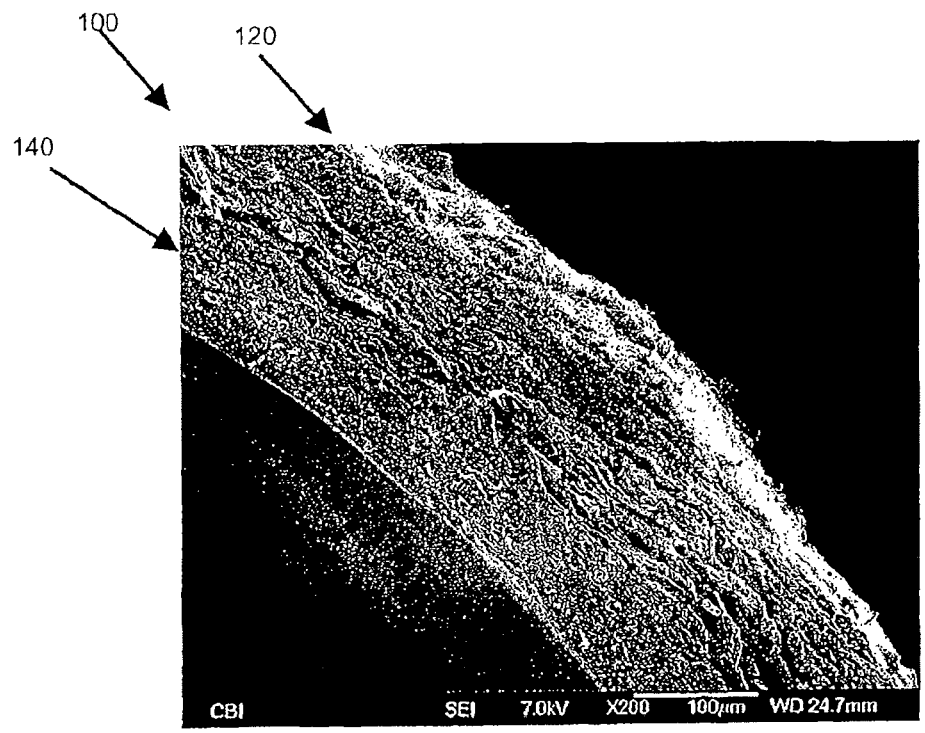
FIGS. 1e and 1f illustrate microscopic photos of a graft device, consistent with the current invention.
Figure 1F:
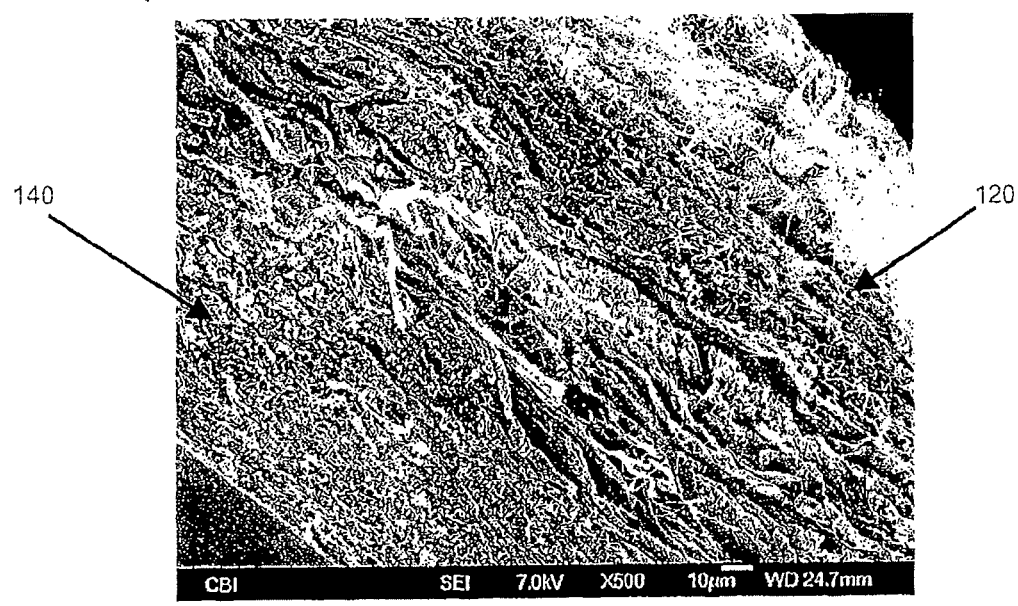

Referring now to FIGS. 1e and 1f microscopic views of a graft device of the present invention is illustrated. Graft device 100 includes tubular member 140 and fiber matrix 120. In the embodiment of FIGS. 1e and 1f, tubular member 140 is a porcine artery, which has fiber matrix 120 surrounding it. Fiber matrix 120 has been electrospun using PEUU, collagen and elastin. Fiber matrix 120 is configured to mechanically and structurally approximate connective tissue. The permeability of fiber matrix 120 allows oxygen and nutrient diffusion to and from tubular member 140. Fiber matrix 120 conformally adjusts to changes in tubular member 140 outer surface, such as during shaping and handling of device 100.

Figure 2:
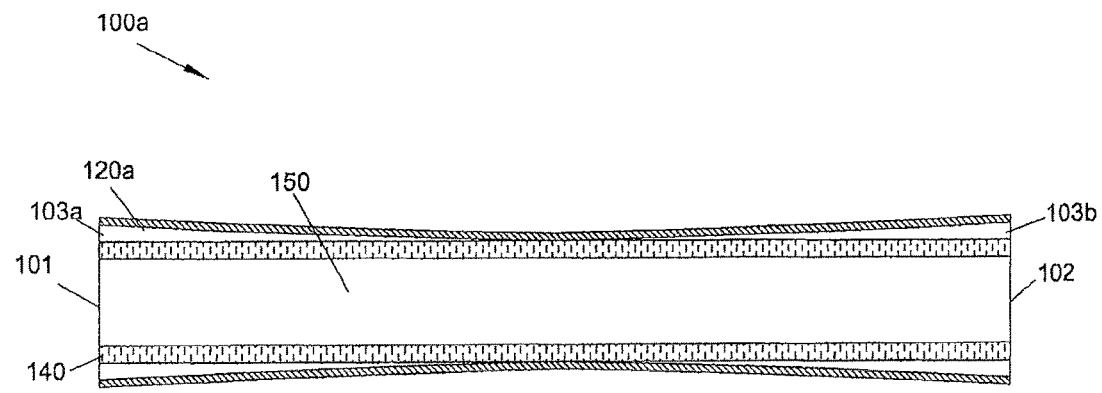
FIG. 2 illustrates a side sectional view of another embodiment of a graft device for a mammalian patient including a tubular member and a surrounding fiber matrix that includes flared ends, consisting with the current invention.

Referring now to FIG. 2, a side sectional view of a graft device of the present invention is illustrated including a fiber matrix with a tapered profile. Graft device 100a includes tubular member 140, circumferentially surrounded by fiber matrix 120a. Graft device 100a includes a first end 101, and a second end 102, and is preferably configured to be placed between a first body location and a second body location of a patient, such as the aorta and a diseased coronary artery. Graft device 100a includes lumen 150 from first end 101 to second end 102, such as to carry blood when graft device 100a is connected between the two blood vessels. Fiber matrix 120a is preferably applied using an electrospinning process, as has been described in detail hereabove. Fiber matrix 120a has a tapered profile at each end, such that there are spaces 103a between fiber matrix 120a and tubular member 140 at end 101 and space 103b between fiber matrix 120a and tubular member 140 at end 102. In a typical surgical anastomotic procedure, the surgeon spatulates one or more ends of a graft to improve the anastomotic connection. The flared ends of fiber matrix 120a are configured to accommodate flaring or other radial expansion of the ends of device 100, such as in the performing of the anastomosis, avoiding any undesired stretch to fiber matrix 120a (i.e. tubular member 140 expands into space 103, such that the restrictive force applied by fiber matrix 120a remains relatively uniform after anastomosing of the tubular member 140 ends. In a preferred embodiment, a tapered member is used during the electrospinning process, not shown but placed at each end of tubular member 140 to cause spaces 103 to result. The tapered members may be configured to dissolve or be manually removed prior to implantation of graft device 100a. It should be understood that while the taper of fiber matrix 120a is shown as symmetric, asymmetric tapering can be achieved such as when the diameter of tubular member 140 is different at end (i.e. such as to have equal spaces 103 to accommodate equal expansion of tubular member 140, such as during the creation of an anastomosis). In an alternative embodiment, one or more ends taper radially in, such as to create a smaller diameter fiber matrix at one or both ends of device 100a. In another alternative embodiment, fiber matrix 120 is applied to tubular member 140 in loose fashion, such as where the inside diameter of the fiber matrix is somewhat larger than the outside diameter of tubular member 140 along all a portion of the length of device 100a. In this particular configuration, radial constriction of tubular member 140 does not begin until the outside diameter of tubular member 140 approaches the inside diameter of fiber matrix 120. In yet another alternative embodiment, fiber matrix 120 is applied to tubular member 140 in pre-constricting geometry, such as where the inside diameter of the fiber matrix is somewhat smaller than the outside diameter of tubular member 140 along all portions of the length of device 100a. In this particular configuration, radial constriction of tubular member 140 occurs prior to implantation, such as to reduce the caliber (luminal cross section) of tubular member 140.

Figure 3:
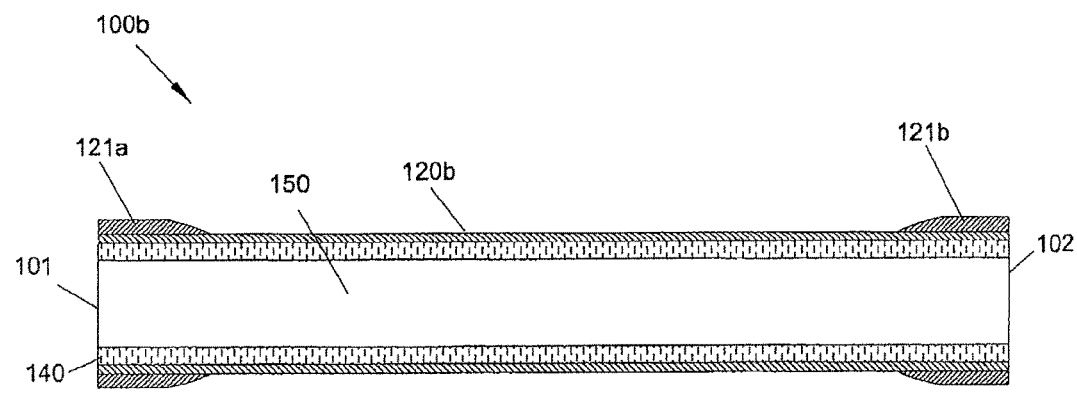
FIG. 3 illustrates a side sectional view of yet another embodiment of a graft device for a mammalian patient including a tubular member and a surrounding fiber matrix that includes reinforced ends, consisting with the current invention.

Referring now to FIG. 3, a side sectional view of a graft device of the present invention is illustrated including a fiber matrix with reinforced end portions. Graft device 100b includes tubular member 140, circumferentially surrounded by fiber matrix 120b. Graft device 100b includes a first end 101, and a second end 102, and is preferably configured to be placed between a first body location and a second body location of a patient, such as the aorta and a diseased coronary artery. Graft device 100b includes lumen 150 from first end 101 to second end 102, such as to carry blood when graft device 100 is connected between the two blood vessels. Fiber matrix 120b is preferably applied using an electrospinning process, as has been described in detail hereabove. Fiber matrix 120b has a reinforced portion at each end, reinforcement 121a and end 101 and reinforcement 121b at end 102, each configured to provide additional strength to the ends 101 and 102, such as to improve an anastomotic connection.

In a typical embodiment, reinforcements 121a and 121b are simply thicker portions of fiber matrix 120b, additional thickness achieved in one or more processes described in detail hereabove. Alternatively or additionally, reinforcements 121a and 121b may include a different fiber material or a different matrix of the same or different fibers, also as has been described in detail hereabove. In some embodiments, a material such as a mesh or felt material made of a biological-based or synthetic-based material, with or without surface functionalization, either biodegradable or not, for example a Dacron mesh, is included in reinforcements 121a or 121b. The mesh may be added before, during or after the fiber matrix application, and may be located under, within or on top of the fiber matrix.

Reinforcements 121a and 121b may be biodegradable, such as when fiber matrix 120b is biodegradable. Reinforcements 121a and 121b may include numerous features configured to achieve an improved anastomotic connection such features selected from the group consisting of: a thicker matrix; a thinner matrix; a band such as a needle penetrable band; a matrix with flared ends; an adhesive surface configured to temporarily or permanently assist in anastomotic coupling; a hook and/or loop component similar to Velcro and configured to mate with a corresponding component at the anastomotic site; a magnetic component configured to mate with a corresponding magnetic component at the anastomotic site; and combinations of these. Reinforcements 121a or 121b may include one or more holes configured for passing of anastomotic sutures or clips. Alternatively or additionally, reinforcements 121a or 121b may include one or more extending loops, not shown but configured to aid in anastomotic suturing or clipping. The loops may be integrated into the fiber matrix, or applied after an electrospinning process.

It should be understood that while reinforcements 121a and 121b are shown as similar in geometry, different geometries and/or different constructions may be employed such as a first construction configured to optimally achieve an end to side anastomosis to the aorta, and a different geometry configured to optimally achieve an end to side anastomosis to a diseased coronary artery distal to an occlusion.

Graft device 100b further includes an adhesive layer 141 positioned between the outer surface of tubular member 140 and the inner surface of fiber matrix 120. In a preferred embodiment, adhesive layer 141 comprises fibrin glue. Adhesive layer 141 may provide one or more of the following functions: protection of tubular member 140 during the process in which fiber matrix 120 is applied, such as an electrospinning process involving potentially damaging chemicals or temperatures; delivery of a nutrient such as a nutrient contained within adhesive layer 141; delivery of an agent such as a drug contained within adhesive layer 141; and providing a compressible layer between tubular member 140 and fiber matrix 120, such as to allow for vein compliance.

Figure 4:
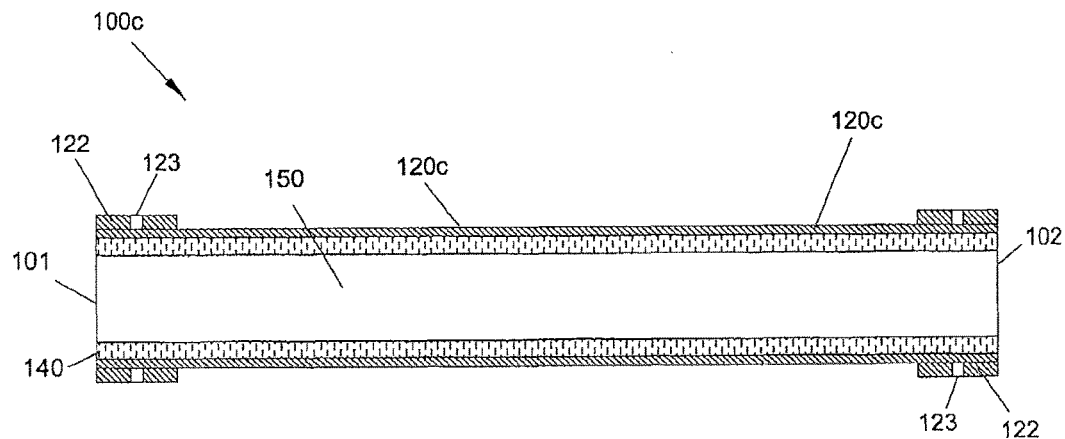
FIG. 4 illustrates a side sectional view of yet another embodiment of a graft device for a mammalian patient including a tubular member and a surrounding fiber matrix that includes a band at each end, consisting with the current invention.

Referring now to FIG. 4, a side sectional view of a graft device of the present invention is illustrated including a fiber matrix with a band at each end. Graft device 100c includes tubular member 140, circumferentially surrounded by fiber matrix 120c. Graft device 100c includes a first end 101, and a second end 102, and is preferably configured to be placed between a first body location and a second body location of a patient, such as the aorta and a diseased coronary artery. Graft device 100c includes lumen 150 from first end 101 to second end 102, such as to carry blood when graft device 100c is connected between the two blood vessels. Fiber matrix 120c is preferably applied using an electrospinning process, as has been described in detail hereabove. Fiber matrix 120c includes circumferential band 122 at each end.

Figure 4A:
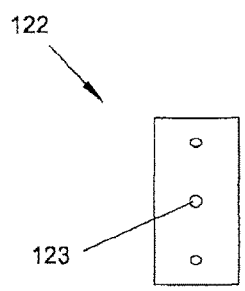
FIGS. 4a and 4b illustrate side and end views, respectively, of the bands of FIG. 4.
Figure 4B:
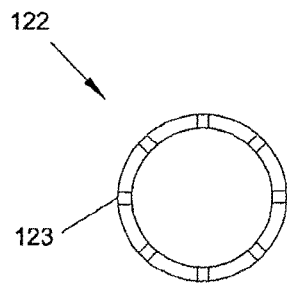

Band 122 includes multiple holes 123 configured to allow an anastomotic clip or suture to pass therethrough. While band 122 is shown attached to the external surface of fiber matrix 120c, in an alternative embodiment band 122 may be located within matrix 120c, between matrix 120c and tubular member 140, or within tubular member 140. Referring additionally to FIGS. 4a and 4b, side and end views of band 122 are shown. Band 122 may be resiliently biased, may be plastically deformable, or may include both resiliently biased and plastically deformable portions. While shown as a circle, band 122 may have different cross sectional geometries such as an elliptical profile. Alternatively, the ends of band 122 may extend evenly beyond the ends of matrix 120c, or eccentrically at some angle relative to the end of tubular member 140. In one embodiment, band 122 is configured to biodegrade over a period of hours to months. In another embodiment, fiber matrix 120c is biodegradable, but band 122 is configured to remain, such as when band 122 is resiliently biased to constrict around tubular member 140 as fiber matrix 120c biodegrades.

Figure 5:
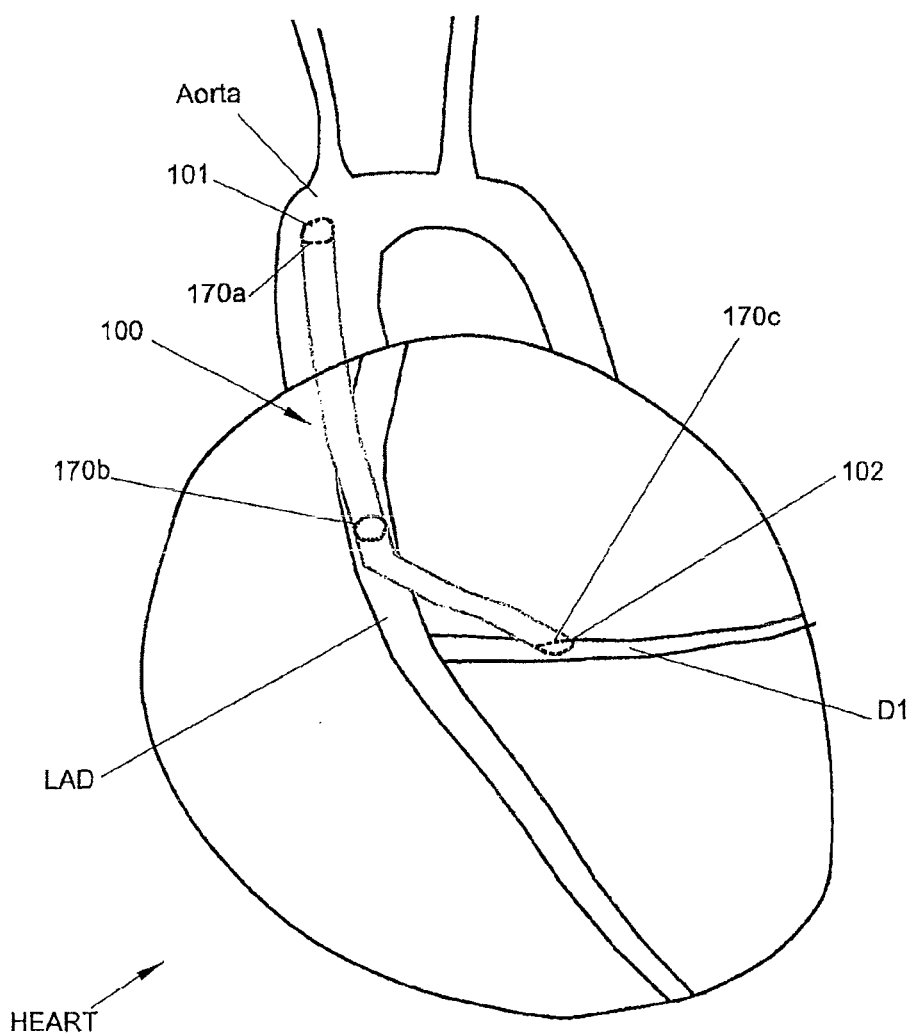
FIG. 5 illustrates a side view of a heart and aorta of a mammalian patient with a graft of the current invention attached to multiple vessels in a serial connection scheme.

Referring now to FIG. 5, a side view of a heart and aorta of a mammalian patient with a graft of the current invention attached to multiple vessels in a serial connection scheme is shown. Graft device 100 includes first end 101 and second end 102. First end 101 is fluidly attached to the aorta at connection 170a, an end to side anastomosis. A midportion of graft device 100 is fluidly attached to the left anterior descending artery (LAD) at connection 170b, a side to side anastomosis. Second end 102 is fluidly attached to a diagonal of the LAD, D1, at connection 170c, another end to side anastomosis. Device 100 is serially attached to the patient's heart such that blood flows from the aorta into the LAD at connection 170b, and into D1 at connection 170c. An advantage of the serial connection scheme shown in FIG. 5 is that the flow through the portion of device 100 between connection 170a and 170b is increased due to the additional flow into connection 170c. Higher flow has been shown to improve patency of vein grafts in patients in numerous studies. In one embodiment, graft device 100 comprises a fiber matrix surrounding a vessel graft, such as a harvested saphenous vein graft. The serial connection 170b is made at a location along the vein graft that previously included the ostium to or from a side branch of a harvested artery or vein. In other words, the opening in the side of the vein graft becomes the anastomosis site, yielding improved flow conditions. Device 100's fiber matrix is created such as to keep the side branch site intact. A hole punch or other tool is used to make the corresponding opening in the fiber matrix. Numerous combinations of anastomosis and serial connections with one or more additional devices 100, such as a first device connected in an end to side anastomosis to a second device, can be used to achieve a desired flow configuration.

Figure 6:
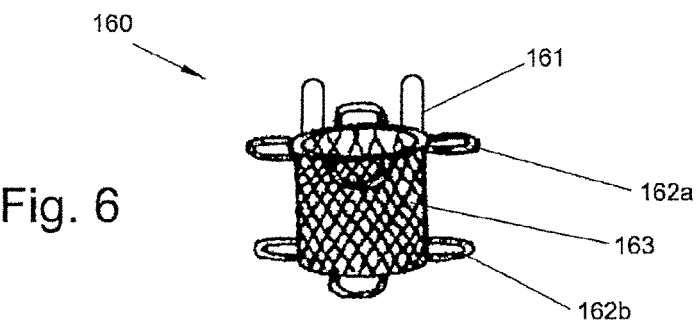
FIG. 6 illustrates a side view of an anastomotic connector, consistent with the current invention.

Referring now to FIG. 6, an anastomotic connector of the present invention is illustrated. Connector 160 includes axial projections 161, configured to be mated or otherwise attached to a graft device of the present invention to improve the connecting of the graft device to a blood vessel in an end to side anastomosis. Connector 160 also includes midportion 163 which is attached at one end to axial projections 161, and at both ends to radial projections 162a and 162b. Axial projections 161 are configured to mate with a graft device of the present invention. Radial projections 162a and 162b are configured to assist in the creation of an end to side anastomotic connection, such as to reside inside and outside a vessel wall at the anastomosis. In a preferred embodiment, axial projections 161 and/or radial projections 162a and 162b are flexibly attached to midportion 163 such as to accommodate flexion during creation of the anastomosis or after implantation.

Figure 6A:
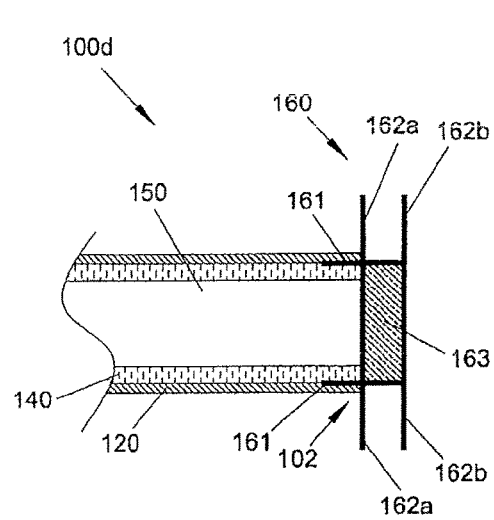
FIG. 6a illustrates a side sectional view of the anastomotic connector of FIG. 6 with axial projections between a tubular member and fiber matrix, consistent with the current invention.

Referring now to FIG. 6a, the anastomotic connector of FIG. 6 is illustrated integral to a graft device of the present invention. Graft device 100d includes tubular member 140, fiber matrix 120 and lumen 150, as have been described in detail hereabove. Connector 160 includes midportion 163, as well as connected axial projections 161 and radial projections 162a and 162b. At end 102, axial projections 161 of connector 160 are located between fiber matrix 120 and tubular member 140. In one embodiment, connector 160 is positioned at end 102 so that as fiber matrix 120 is applied, via electrospinning, axial projections 161 are captured between fiber matrix 120 and tubular member 140, or axial projections 161 are captured within fiber matrix 120 (i.e. inserted part way into electrospinning process). In an alternative embodiment, axial projections 161 may be inserted between fiber matrix 120 and tubular member 140 after fiber matrix 120 has been applied to tubular member 120. In still another embodiment, the end of connector 160 is configured at an angle other than 90 degrees to the longitudinal axis of tubular member 140, thus allowing the connection between the tubular member and anastomosed blood vessel to be at a similar angle, thus reducing turbulence and/or reducing pressure caused by impingement of blood flow into the side wall of the anastomosed vessel.

Figure 6B:
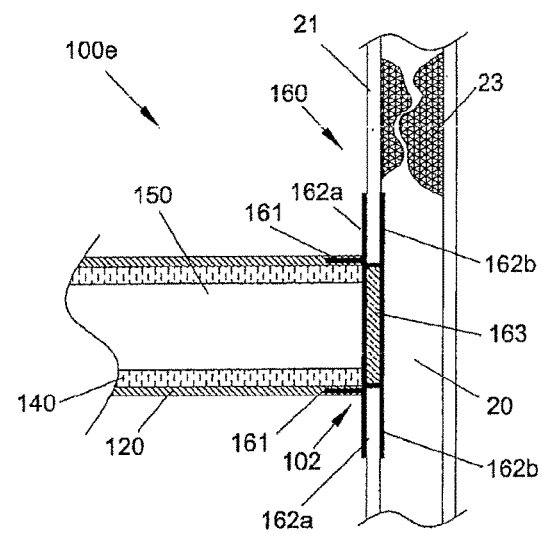
FIG. 6b illustrates a side sectional view of the anastomotic connector of FIG. 6, with axial projections within a fiber matrix and attached distal to an occluded artery, consistent with the present invention.

Referring now to FIG. 6b, the anastomotic connector of FIG. 6 is illustrated integral to a graft device of the present invention. Graft device 100e includes tubular member 140, fiber matrix 120 and lumen 150, as have been described in detail hereabove. Connector 160 includes midportion 163, as well as connected axial projections 161 and radial projections 162a and 162b. Axial projections 161 of connector 160 are located at end 102 within fiber matrix 120, such as when axial projections 161 are positioned above a partially applied fiber matrix 120 (e.g., part way through the electrospinning process) subsequent to which the fiber matrix application is completed, capturing axial projections 161.

Graft device 100c has been connected to artery 20 via an end to side anastomosis using connector 160. Radial projections 162a reside on the exterior side of arterial wall 21, while radial projections 162b reside on the interior side of arterial wall 21. Connector 160 is positioned distal to occlusion 23 of artery 20, such that blood flowing through lumen 150 of graft device 100e flows distally in artery 20 away from occlusion 23.

Figure 7:
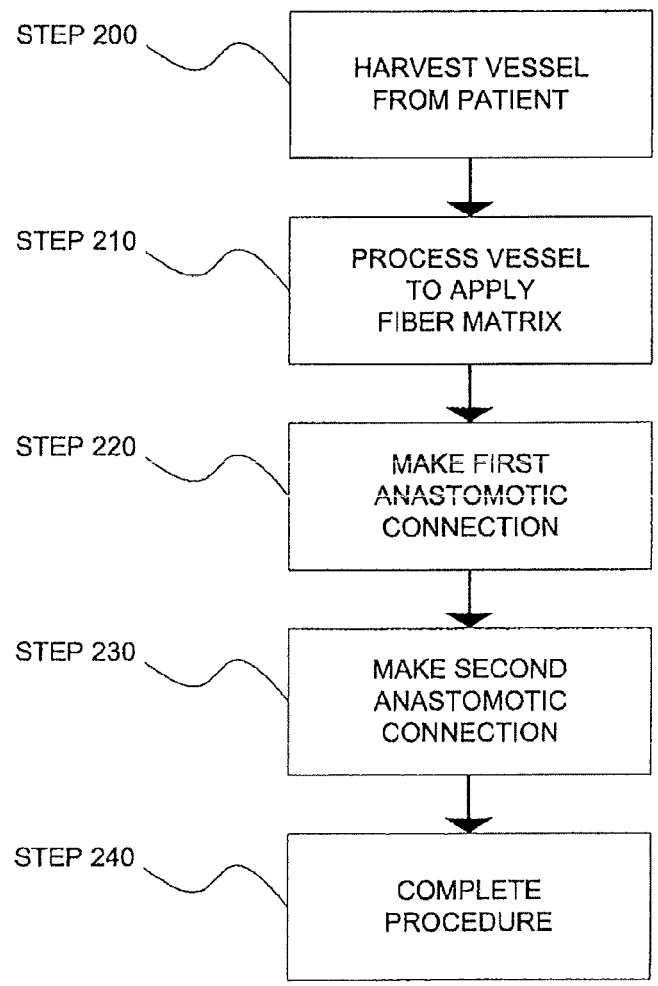
FIG. 7 is a flow chart of a preferred method of harvesting a vessel, producing a graft device of the present invention, and attaching the graft device to two or more body spaces, consistent with the present invention.

Referring now to FIG. 7, a preferred method of selecting, manufacturing and placing a graft device of the present invention is illustrated. Step 200 includes the harvesting of a vessel such as a saphenous vein portion harvested using an open surgical or minimally invasive procedure. The harvested vessel may include one or more side branches that are removed and their fluid pathway ligated or otherwise closed, preferably without the inclusion of metal clips or other metal components that may interfere with one or more subsequent processes, such as electrospinning. Multiple vessel portions may be harvested or a single portion may be divided into multiple segments. One or both ends of the vessel may be cut, orthogonally or at some oblique angle or curvilinear pattern, such as to form a custom shape or refine end conditions of the graft.

Step 210 includes the application of a fiber matrix on the harvested vessel. In a preferred embodiment, electrospinning, in the one or more configurations described hereabove, is used to apply the fiber matrix. The application may be dependent on one or more patient parameters, such as a parameter associated with the harvested vessel, for example the geometry of the harvested vessel; a parameter associated with one or more vessels to which the graft device is to be fluidly connected, for example the number or type of side branches; or another patient parameter, for example the patient's age. Application may be applied to a single vessel segment or multiple segments simultaneously. The fiber matrix may be applied in a relatively uniform geometry, or a varied geometry such as a fiber matrix with modified end portions such as thicker end portions or end portions with a smaller or larger diameter than midportions of the graft.

After the fiber matrix has been applied, one or both ends of the graft device may be cut. One or both ends may be spatulated such as to improve the anastomotic connection. If one or more graft devices ends include a reinforcing portion or integral anastomotic connector, cutting will be avoided.

Referring now to Step 220, a first anastomotic connection is made between an end of the graft device (e.g., in an end to side anastomosis) or a midportion of the graft device (e.g., in a side to side anastomosis). The graft may include improved anastomotic connection ends, such as ends including one or more of: a thicker matrix; a thinner matrix; a multiple fiber-type matrix; a flared end matrix; a hook and loop component similar to Velcro; an adhesive surface; and an embedded magnetic component on or in the matrix. The anastomosis may be performed in an open surgical procedure, in a minimally invasive surgical procedure, or in a percutaneous procedure such as a procedure in which the graft device is introduced over a guidewire. The anastomosis is typically performed with suture and/or surgical clips, such as suture passed through a reinforced end of the fiber matrix. The graft may include an integral anastomotic connector, or an anastomotic connector may be attached to the graft device at the time of surgery (as described in reference to FIGS. 6a and 6b).

Referring now to Step 230, a second anastomotic connection is performed, such as an end to side anastomosis or a side to side anastomosis. In a preferred embodiment, two anastomotic connections are used (Step 220 and Step 230), an end to side connection to the aorta and an end to side connection to a coronary artery distal to an occlusion. In another preferred embodiment, a third anastomotic connection is performed, such that a serial grafting procedure is accomplished including a side to side anastomosis at a mid portion of the device, and an end to side anastomosis at each graft device end. For cardiac bypass surgery, a first end of the graft device is attached to a source of arterial blood, such as with an anastomosis to the side of the aorta, an internal mammary artery, or another graft. A second end of the graft device, and potentially one or more midportion locations, are fluidly attached to one or more occluded arteries, downstream of the occlusion.

In an alternative embodiment, prior to performing the second anastomosis, the fiber matrix is removed. A second fiber matrix may be applied, such as when the graft device is unattached, or the harvested vessel without the fiber matrix may be implanted.

In Step 240, the procedure is completed. In cardiac bypass procedures, the patient may be placed on a circulatory bypass pump and/or heart-lung machine and the heart may be stopped while the anastomoses are being created. After fluid connections are complete, the heart will be restarted (if stopped) and the anastomotic connections checked for issues. In an off-pump procedure the anastomoses might be made with the help of intra-coronary shunts devices, which are removed just prior to completion of the anastomosis.

Surgical incisions and penetrations will be closed with suture, staples and other closure devices.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed:

1. A graft device for a mammalian patient, the graft device comprising:
   a) a tubular member comprising a first end and a wall surrounding a lumen, the wall having an outer surface comprising a series of non-circular cross sections varying at least in part over a portion of a length of the tubular member; and
   b) a fiber matrix surrounding the tubular member comprising a deposition coating of polymer fibers deposited onto, formed along, and conforming to the outer surface of a mid portion of the tubular member, the fiber matrix having an inner circumferential surface substantially contiguous with the series of non-circular cross sections of the outer surface of the mid portion of the tubular member,
   wherein the fiber matrix comprises a first end, a mid portion, a second end and an asymmetric thickness profile from the first end of the fiber matrix to the second end of the fiber matrix.

2. The device of claim 1, wherein the first end of the fiber matrix has a different thickness than the second end of the fiber matrix.

3. The device of claim 1, wherein the tubular member has the first end, a second end, and a thickness profile from the first end of the tubular member to the second end of the tubular member, and the thickness profile of the fiber matrix is based on the thickness profile of the tubular member.

4. The device of claim 1, wherein the mid portion of the fiber matrix comprises a thickness greater than a thickness of the first end of the fiber matrix, the second end of the fiber matrix, or a combination thereof.

5. The device of claim 1, wherein a thickness of the first end of the fiber matrix or the second end of the fiber matrix is greater than a thickness of the mid portion of the fiber matrix.

6. The device of claim 1, wherein the first end of the fiber matrix is configured to form an anastomotic connection to a vessel proximate an aorta.

7. The device of claim 1, wherein the mid portion of the fiber matrix is configured to form an anastomotic connection to an arterial vessel.

8. The device of claim 1, wherein the graft device is configured to form three anastomotic connections.

9. The graft device of claim 1, wherein the fiber matrix comprises a matrix of electrospun fibers.

10. The graft device of claim 1, wherein the tubular member comprises tubular tissue.

11. The graft device of claim 10, wherein the tubular member comprises a conduit selected from the group consisting of: vein; artery; urethra; intestine; esophagus; ureter; trachea; bronchi; duct; fallopian tube; and combinations thereof.

12. The graft device of claim 1, wherein the tubular member comprises a vein segment.

13. The graft device of claim 1, wherein the tubular member comprises a segment of saphenous vein.

14. The graft device of claim 1, wherein the first end of the fiber matrix comprises a reinforced portion of the fiber matrix.

15. The graft device of claim 14, wherein the reinforced portion comprises an increased thickness portion of the fiber matrix.

16. The graft device of claim 1, further comprising an anastomotic connector positioned at at least one of the following regions: i) within the tubular member; ii) on the fiber matrix; or iii) within the first end of the fiber matrix.

17. The graft device of claim 1, wherein the fiber matrix comprises an average pore size between about 10 microns and about 1,000 microns.

18. The graft device of claim 1, wherein the fiber matrix comprises an average pore size between about 100 microns and about 500 microns.

19. The graft device of claim 1, wherein the fiber matrix comprises a porosity between about 50% and about 95%.

20. The graft device of claim 1, wherein the fiber matrix comprises a porosity between about 60% and about 95%.

* * * * *